United States Patent [19]

Nusslein et al.

[11] 4,061,645

[45] Dec. 6, 1977

[54] 2-TRICHLOROMETHYL-5-METHYLSULFI-NYL-1,3,4-THIADIAZOLE

[75] Inventors: Ludwig Nüsslein; Ernst Albrecht Pieroh; Kurt Röder, all of Berlin, Germany

[73] Assignee: Schering Aktiengesellschaft, Berlin & Bergkamen, Germany

[21] Appl. No.: 298,274

[22] Filed: Oct. 17, 1972

Related U.S. Application Data

[63] Continuation of Ser. No. 883,253, Dec. 8, 1969, abandoned.

[51] Int. Cl.$^2$ .......................................... C07D 285/12

[52] U.S. Cl. .............................. 260/302 SD; 424/270
[58] Field of Search .................................. 260/302 SD

[56] References Cited

U.S. PATENT DOCUMENTS

| | | | |
|---|---|---|---|
| 3,562,284 | 2/1971 | Newman et al. | 260/302 SD |
| 3,692,794 | 9/1972 | Rosen et al. | 260/302 SD |

Primary Examiner—R. J. Gallagher

[57] ABSTRACT

New 1,3,4-thiadiazoles substituted in the 2 and 5 positions for use as soil and seed fungicides, nematocides and the processes therefor.

1 Claim, No Drawings

2-TRICHLOROMETHYL-5-METHYLSULFINYL-1,3,4-THIADIAZOLE

This is a continuation of application Ser. No. 883,253, filed Dec. 8, 1969, now abandoned.

This invention relates to new 1,3,4-thiadiazoles, substituted in 2 and 5 position, the use thereof as soil and seed fungicides and as nematocides, as well as processes for the production of the active ingredients.

Fungicidal substances on the basis of 1,2,4-thiadiazole have become known (U.S. Pat. Nos. 3,260,588 and 3,260,725). 5-ethoxy-3-trichloromethyl-1,2,4-thiadiazole, distinguished by a special fungicidal effectiveness, has, however, only a specific effectiveness against Pythium.

The object underlying the present invention was to develop an agent effective especially against Pythium, Rhizoctonia, Fusarium and other fungi and pests.

It has now been found that compounds of the general formula

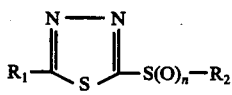

wherein $R_1$ is a low halogen alkyl, preferably halogen methyl; $R_2$ is an aliphatic hydrocarbon radical with preferably 1 to 8 carbon atoms; and $n$ is 1 or 2, are in particular very effective fungicides against harmful fungi living in the soil, on seed and other plant parts.

In the fungicidally efffective dose, the claimed compounds are essentially not poisonous, so that they can readily be applied on seed or be used together with seed. Since they exhibit, moreover, a good plant tolerance, damage to crop plants can be precluded to a large extent when using them.

The compounds are effective, among others, against Pythium, Rhizoctonia, Fusarium, Tilletia, Helminthosporium, as well as against Venturia, Plasmopara, Botrytis and other injurious fungi.

It has further been found that the compounds are nematocidal and bactericidal. Compounds containing a radical $R_1$ symbolizing trifluoromethyl show, in particular in the vapor or gaseous phase, an excellent fungicidal effectiveness which, referred to the volume of air, is approximately 1 ppm.

Particularly suitable compounds, for example are as follows:
2-trifluormethyl-5-methylsulfonyl-1,3,4-thiadiazole,
2-dichloromethyl-5-methylsulfinyl-1,3,4-thiadiazole,
2-trichloromethyl-5-methylsulfinyl-1,3,4-thiadiazole,
2-dichloromethyl-5-methylsulfonyl-1,3,4-thiadiazole,
2-trichloromethyl-5-methylsulfonyl-1,3,4-thiadiazole,
2-trichloromethyl-5-propylsulfinyl-1,3,4-thiadiazole,
2-dichloromethyl-5-propylsulfonyl-1,3,4-thiadiazole,
2-dichloromethyl-5-ethylsulfinyl-1,3,4-thiadiazole,
2-trifluromethyl-5-ethylsulfonyl-1,3,4-thiadiazole,
2-trifluoromethyl-5-methylsulfinyl-1,3,4-thiadiazole,
2-trifluormethyl-5-ethylsulfinyl-1,3,4-thiadiazole,
2-trifluoromethyl-5-isopropylsulfinyl-1,3,4-thiadiazole, and
2-trifluoromethyl-5-isopropylsulfonyl-1,3,4,-thiadiazole.

Because of their broad fungicidal effectiveness, the compounds according to the invention are superior not only to the known 1,2,4-thiadiazole derivative, but also to agents on a basis of zinc-ethylene-bis-dithiocarbamate, 1,4-dichloro-2,5-dimethoxybenzene, pentachloronitrobenzene, N-(trichloromethylthio)-cyclohex-4-ene-1,2-dicarboximide. Therefore, they permit a reliable control of said fungi.

Moreover, since the compounds exhibit a very low toxicity to warm-blooded animals, the acute oral toxicity ($LD_{50}$) of 2-trichloromethyl-5-methyl-sulfonyl-1,3,4-thiadiazole in rats is, for example, 717 mg/kg - the application can be made relatively without danger.

The compounds can, therefore, be used in agriculture and horticulture for general soil treatment, seed treatment or for furrow treatment. The action is directed not only to damaging fungi which attack from the soil, but also to those which are transmitted by seed and parasites on the above-ground plant parts. Surprisingly, the fungicidal ingredients according to the invention show in part systemic properties. With the application of the invention, soil-inhabiting nematodes are controlled and bacteria destroyed.

The active ingredients may be used alone or mixed with one another, or if desired, with other plant protecting or pest control agents, e.g., with insecticides, if the simultaneous control of these or other pests is desired. Also, the addition of synergistic substances is possible.

Application is effected expediently as powder, scatter material, granules, solution, emulsion or suspension, or as aerosols, with the addition of solid and/or liquid diluents or vehicles and possibly of adhesive, wetting, emulsifying and/or dispersing aids.

Suitable liquid vehicles are, for example, water, mineral oils or other organic solvents, such as xylene, chlorobenzene, chloroform, 1,3-dichloroprene, cyclohexanone, ether, acetic ester, dimethyl formamide, dimethyl sulfoxide, ethylene dibromide and 1,2-dichloro-3-bromopropane, etc.

Suitable solid vehicles are lime, attaclay and other clays, kaolin, talcum, as well as natural or synthetic silica, etc.

Surface-active substances suitable for use in the invention are salts of the lignin-sulfonic acids, salts of alkylated benzene-sulfonic acids, sulfonated acid amides and their salts, polyethoxylated amines and alcohols.

If the active substances are to be used for seed disinfection, dyes, such as new fuchsine, etc., may be admised to give the disinfected seed a clearly visible coloration.

The proportion of active substance or substances in the agent may vary within wide limits, the exact concentration of the active ingredient used for the agents depending mainly on the quantity in which the agents are to be used for soil or seed treatment, etc. As an example, the agents contain between about 0.1 and 80 percent by weight, preferably between about 10 and 50 percent by weight, of active ingredient and about 99 to 20 percent by weight of liquide or solid vehicles and possibly up to 20 percent by weight of liquid or solid vehicles and possibly up to 20 percent by weight of surface-active substances. The production of the various forms of preparation is effected as known in the art, such as by grinding or mixing processes. What is remarkable is that the active substances are excellently suitable for dry disinfectants of low active ingredient content.

To promote germination of the seed, the agents are applied in the usual manner either before sowing directly on the seed or during sowing the furrow (so-called tilling-in). For treatment of the soil itself, the agents are expediently introduced in the upper soil layers to a depth of about 20 cm, e.g., by hoeing in.

In the compounds designated in the above general formula, it must be understood that low alkyl radicals containing up to 7 carbon atoms, mono- or multi-fluorinated, -chlorinated or -brominated with $R_1$, or these radicals may be substituted with various halogen atoms. Among these compounds, those with mono-, di- or tri-halogen methyl radicals, such as monochloromethyl, dichloromethyl, trichloromethyl, monobromomethyl, dibromomethyl or trifluoromethyl are outstanding.

As aliphatic hydrocarbon radicals $R_2$ are preferably those containing 1 to 8 carbon atoms, in particular straight-chain or branched alkyl radicals, as for example, methyl, ethyl, propyl, isopropyl, butyl, pentyl, hexyl, heptyl and octyl radicals, etc.

$n$ may signify 1 or 2 in the general formula.

The previously unknown compounds may be produced, for example, by the action of oxidation agents on corresponding 5-mercapto-1,3,4-thiadiazoles of the general formula

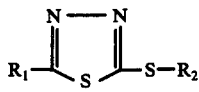

wherein the radicals $R_1$ and $R_2$ have the above indicated meaning.

For the production of compounds of this general formula, there may be used as oxidizing agents, if $n = 1$, for example organic hydroperoxides, such as tertiary butyl hydroperoxide, or m-chloroperbenzoic acid, and the like, or inorganic reagents, such as hydrogen peroxice, sodium-m-periodate, and the like. Advantageously one takes for this two oxidation equivalents of the oxidizing agent per mole of the mercapto compound at temperatures of about +40° to 0° C.

For the production of compounds with $n$ meaning 2, there may be used, besides the oxidizing agents already named, inorganic reagents such as potassium permananate, chromic acid or their salts, or nitric acid, in the temperature range from about 0° to 120° C. Per mole of mercapto compound, there are taken for this four oxidation equivalents, that is, twice as much as is required for the above described sulfoxidation.

As reaction media, there may be used, if desired, organic solvents such as acetic acid, dioxane, ketones, acetone or others, and this either alone or in mixture with water.

The following examples explain the production of the compounds.

a. 24.9 g of 2-trichloromethyl-5-methylmercapto-1,3,4-thiadiazole are dissolved in 200 ml of glacial acetic acid, 11.3 g of a 30% hydrogen peroxide being added drop by drop and left standing over night. The mixture is then concentrated under vacuum, the residue taken up in methylene chloride, the remaining acetic acid is removed with dilute soda solution, the resultant residue is dried in the organic phase, concentrated and recrystallized from a small amount of isopropyl ether.

Yield: 23.4 g or 88% of the theory of 2-trichloromethyl-5-methylsulfinyl-1,3,4-thiadiazole, m.p. 89°-90° C.

b. Into a solution of 107.6 g of 2-dichloromethyl-5-methylmercapto-1,3,4-thiadiazole in 750 ml of glacial acetic acid and 300 ml of water slowly put 105.5 g of potassium permanganate, by portions. During charging, the temperature is maintained at 10° C while vigorously agitating. Let react at the same temperature for another 30 minutes, then add 2.5 liter of water, and reduce the percipitated $MnO_2$ between 0° and 5° C with a solution consisting of 95 g of sodium metabisulfite in 400 ml of water. When almost the entire amount has been dropped in, the reduction is completed with decoloration. Suction off the precipitated substance, wash with water, and recrystallize from about 170 ml of isopropanol.

Yield: 92 g, corrsponding to 74% of theory of 2-dichloromethyl-5-methyl-sulfonyl-1,3,4-thiadiazole, m.p. 75° C.

c. Into a solution of 36.75 g of 2-dichloromethyl-5-ethylmercapto-1,3,4-thiadiazole in 200 ml of chloroform slowly charge, while stirring and cooling with 28.5 g of m-chloroperbenzoic acid. Let react for another hour, extract the m-chlorobenzoic acid with dilute soda solution, wash with water, and dry over magnesium sulfate. After evaporation of the solvent, recyrstallize, from little isopropyl ether.

Yield: 33 g corresponding to 88% of the theory of 2-dichloromethyl-5-ethyl-sulfonyl-1,3,4-thiadiazole, m.p. 75° C.

Additinal compounds according to the invention are listed in the following table.

| Compound No. | Name of Compound | Physical Constant |
|---|---|---|
| 1 | 2-trifluoromethyl-5-methylsulfonyl-1,3,4-thiadiazole | m.p. 88° C |
| 2 | 2-chloromethyl-5-methylsulfinyl-1,3,4-thiadiazole | $n_D^{20} = 1.5911$ |
| 3 | 2-dichloromethyl-5-methylsulfinyl-1,3,4-thiadiazole | m.p. 86° C |
| 4 | 2-dichloromethyl-5-ethylsulfinyl-1,3,4-thiadiazole | m.p. 61° C |
| 5 | 2-dichloromethyl-5-propylsulfinyl-1,3,4-thiadiazole | $n_D^{20} = 1.5703$ |
| 6 | 2-dichloromethyl-5-isopropylsulfinyl-1,3,4-thiadiazole | m.p. 60° C |
| 7 | 2-dichloromethyl-5-amylsulfinyl-1,3,4-thiadiazole | $n_D^{20} = 1.5541$ |
| 8 | 2-trichloromethyl-5-methylsulfinyl-1,3,4-thiadiazole | m.p. 89° C |
| 9 | 2-trichloromethyl-5-ethylsulfinyl-1,3,4-thiadiazole | $n_D^{20} = 1.5830$ |
| 10 | 2-trichloromethyl-5-propylsulfinyl-1,3,4-thiadiazole | $n_D^{20} = 1.5740$ |
| 11 | 2-trichloromethyl-5-isopropylsulfinyl-1,3,4-thiadiazole | $n_D^{20} = 1.5743$ |
| 12 | 2-trichloromethyl-5-butylsulfinyl-1,3,4-thiadiazole | $n_D^{20} = 1.5652$ |

-continued

| Compound No. | Name of Compound | Physical Constant |
|---|---|---|
| 13 | 2-trichloromethyl-5-heptylsulfinyl-1,3,4-thiadiazole | $n_D^{20} = 1.5391$ |
| 14 | 2-trichloromethyl-5-octylsulfinyl-1,3,4-thiadiazole | $n_D^{20} = 1.5380$ |
| 15 | 2-chloromethyl-5-methylsulfonyl-1,3,4-thiadiazole | m.p. 50° C |
| 16 | 2-chloromethyl-5-isopropylsulfonyl-1,3,4-thiadiazole | $n_D^{20} = 1.5482$ |
| 17 | 2-dichloromethyl-5-methylsulfonyl-1,3,4-thiadiazole | m.p. 75° C |
| 18 | 2-dichloromethyl-5-ethylsulfonyl-1,3,4-thiadiazole | m.p. 76° C |
| 19 | 2-dichloromethyl-5-propylsulfonyl-1,3,4-thiadiazole | $n_D^{20} = 1.5554$ |
| 20 | 2-dichloromethyl-5-isopropylsulfonyl-1,3,4-thiadiazole | m.p. 58° C |
| 21 | 2-trichloromethyl-5-methylsulfonyl-1,3,4-thiadiazole | m.p. 123° C |
| 22 | 2-trichloromethyl-5-ethylsulfonyl-1,3,4-thiadiazole | $n_D^{20} = 1.5593$ |
| 23 | 2-trichloromethyl-5-propylsulfonyl-1,3,4-thiadiazole | m.p. 78° C |
| 24 | 2-trichloromethyl-5-isopropylsulfonyl-1,3,4-thiadiazole | m.p. 98° C |
| 25 | 2-trichloromethyl-5-butylsulfonyl-1,3,4-thiadiazole | m.p. 77° C |
| 26 | 2-trichloromethyl-5-amylsulfonyl-1,3,4-thiadiazole | m.p. 50° C |
| 27 | 2-trichloromethyl-5-hexylsulfonyl-1,3,4-thiadiazole | m.p. 47° C |
| 28 | 2-trichloromethyl-5-heptylsulfonyl-1,3,4-thiadiazole | m.p. 54° C |
| 29 | 2-trichloromethyl-5-octylsulfonyl-1,3,4-thiadiazole | m.p. 50° C |
| 30 | 2-bromomethyl-5-methylsulfonyl-1,3,4-thiadiazole | $n_D^{20} = 1.5993$ |
| 31 | 2-bromomethyl-5-ethylsulfonyl-1,3,4-thiadiazole | m.p. 99° C |
| 32 | 2-dibromomethyl-5-methylsulfonyl-1,3,4-thiadiazole | m.p. 113° C |
| 33 | 2-fluoromethyl-5-methylsulfinyl-1,3,4-thiadiazole | m.p. 45° C |
| 34 | 2-fluoromethyl-5-methylsulfonyl-1,3,4-thiadiazole | m.p. 64° C |
| 35 | 2-trifluoromethyl-5-methylsulfinyl-1,3,4-thiadiazole | m.p. 53° C |
| 36 | 2-trifluoromethyl-5-ethylsulfinyl-1,3,4-thiadiazole | $n_D^{20} = 1.4897$ |
| 37 | 2-trifluoromethyl-5-isobutylsulfinyl-1,3,4-thiadiazole | m.p. 54° C |
| 38 | 2-trifluoromethyl-5-pentylsulfinyl-1,3,4-thiadiazole | $n_D^{20} = 1.4801$ |
| 39 | 2-trifluoromethyl-5-hexylsulfinyl-1,3,4-thiadiazole | $n_D^{20} = 1.4790$ |
| 40 | 2-trifluoromethyl-5-ethylsulfonyl-1,3,4-thiadiazole | b.p. 79° C/0.05 Torr |
| 41 | 2-trifluoromethyl-5-isopropylsulfonyl-1,3,4-thiadiazole | m.p. 77° C |
| 42 | 2-trifluoromethyl-5-isobutylsulfonyl-1,3,4-thiadiazole | m.p. 41° C |
| 43 | 2-trifluoromethyl-5-hexylsulfonyl-1,3,4-thiadiazole | m.p. 47° C |
| 44 | 2-trifluoromethyl-5-heptylsulfonyl-1,3,4-thiadiazole | m.p. 64° C |
| 45 | 2-pentafluoroethyl-5-methylsulfonyl-1,3,4-thiadiazole | m.p. 66° C |
| 46 | 2-heptafluoropropyl-5-methylsulfonyl-1,3,4-thiadiazole | m.p. 71° C |
| 47 | 2-(1,1-dichloroethyl)-5-methylsulfonyl-1,3,4-thiadiazole | m.p. 63° C |
| 48 | 2-(1-chloropropyl)-5-methylsulfinyl-1,3,4-thiadiazole | $n_D^{20} = 1.5661$ |
| 49 | 2-(1-chloropropyl)-5-methylsulfonyl-1,3,4-thiadiazole | m.p. 56° C |
| 50 | 2-(1-bromoethyl)-5-methylsulfonyl-1,3,4-thiadiazole | $n_D^{20} = 1.5730$ |
| 51 | 2-(1-bromisobutyl)-5-methylsulfonyl-1,3,4-thiadiazole | $n_D^{20} = 1.5529$ |
| 52 | 2-(1-bromopentyl)-5-methylsulfonyl-1,3,4-thiadiazole | $n_D^{20} = 1.5443$ |
| 53 | 2-(1-bromoisopentyl)-5-methylsulfonyl-1,3,4-thiadiazole | $n_D^{20} = 1.5401$ |

The compounds are soluble in chlorinated hydrocarbons, such as chloroform, 1,3-dichloroprene, etc., ethers, such as dioxane and others, ketones, such as acetone, cyclohexanone, etc., esters, such as acetic ester, etc., acids, such as acetic acid, etc., and dimethylformamide as well as dimethylsulfoxide, etc.

The following examples serve to elucidate and establish the effectiveness of the active substances according to the invention.

EXAMPLE 1

Limit concentrations of the soil-fungicidal effectiveness at homogeneous mixture of the products with the infested soil. Basic condition in the evaluation are a sound root formation without fungus necroses and germination of the seed of at least 90% compared with the result obtained in steamed soil. Per concentration there were seeded 25 grains of peas of the variety "Miracle of Kelvedon" (marrow pea) without a waiting period. The cultivation time in the tests was 20 to 23 days at a temperature of 22°–25° C. Four commercial products were included in the test series.

Pythium ultimum: — Steamed compost soil was inoculated with mycelium of Pythium ultimum Rhizoctania solani: — Steamed compost soil was inoculated with mycelium of Rhizoctonia solani.

Limit concentrations of the fungicidal effectiveness (mg of active substance per liter of soil) determined thus far.

| Compound No. | Pythium ultimum | Rhizoctonia solani |
| --- | --- | --- |
| 1 | 10 mg | 25 mg |
| 2 | 30 mg | 50 mg |
| 3 | 10 mg | 30 mg |
| 4 | 100 mg | 20 mg |
| 5 | 100 mg | 20 mg |
| 6 | over 200 mg | 50 mg |
| 7 | over 200 mg | 50 mg |
| 8 | 20 mg | 10 mg |
| 9 | 200 mg | 10 mg |
| 10 | 100 mg | 20 mg |
| 11 | over 200 mg | 50 mg |
| 12 | 200 mg | 50 mg |
| 13 | over 200 mg | 200 mg |
| 14 | over 200 mg | 100 mg |
| 15 | 10 mg | 100 mg |
| 16 | 150 mg | 200 mg |
| 17 | 10 mg | 20 mg |
| 18 | over 200 mg | 100 mg |
| 19 | 100 mg | 50 mg |
| 20 | 200 mg | 50 mg |
| 21 | 40 mg | 10 mg |
| 22 | 50 mg | 50 mg |
| 23 | 150 mg | 30 mg |
| 24 | 150 mg | 30 mg |
| 25 | over 200 mg | 25 mg |
| 26 | over 200 mg | 25 mg |
| 27 | over 200 mg | 25 mg |
| 28 | over 200 mg | 200 mg |
| 29 | over 200 mg | over 200 mg |
| 30 | 20 mg | 150 mg |
| 31 | 50 mg | over 200 mg |
| 32 | 20 mg | 50 mg |
| 33 | 50 mg | 20 mg |
| 34 | 50 mg | 30 mg |
| 35 | 10 mg | 20 mg |
| 36 | 10 mg | 20 mg |
| 37 | 30 mg | 100 mg |
| 38 | 100 mg | 40 mg |
| 39 | 100 mg | 40 mg |
| 40 | 10 mg | 20 mg |
| 41 | 10 mg | 20 mg |
| 42 | 20 mg | 100 mg |
| 43 | over 100 mg | 50 mg |
| 44 | over 100 mg | 50 mg |
| 45 | 100 mg | over 100 mg |
| 46 | 100 mg | 100 mg |
| 47 | 80 mg | 50 mg |
| 48 | over 100 mg | 100 mg |
| 49 | 100 mg | 50 mg |
| 50 | 40 mg | 100 mg |
| 51 | over 100 mg | 50 mg |
| 52 | no effect | 100 mg |
| 53 | no effect | 100 mg |
| 54 | 10 mg | 20 mg |
| 55 | 10 mg | 10 mg |
| Comparative agents | | |
| 5-ethoxy-3-trichloromethyl-1,2,4-thiadiazole | 20 mg | insufficient effect |
| 1,4-dichloro-2,5 dimethoxybenzene | insufficient effect | 30 mg |
| Pentachloronitrobenzene | insufficient effect | 75 mg |
| N-(trichloromethylthio)-cyclohex-4-ene-1,2-dicarboximide | 300 mg | 300 mg |

The superiority of the compounds according to the invention over the known fungicides is evident from the test data above given.

EXAMPLE 2

Steamed compost soil was inoculated with mycelium of Pythium ultimum. After a homogeneous mixture of the products with the infested soil, the products were in the form of 20% powder preparations, the seeding of 25 grains of marrow peas of the variety "Miracle of Kelvedon" per concentration was effected without a waiting period in clay dishes holding 1 liter of soil. The following table lists the number of germinated sound peas, the weight of the fresh plant, and a root evaluation after a cultivation period of three weeks at 22°–25° C.

Root evaluation: 4 = white roots, without fungus necroses
3 = white roots, slight fungus necroses
2 = brown roots, more intense fungus necroses
1 = severe fungus necroses, roots rotted

| Compound No. | mg of active ingr. per liter of soil | Number of sound peas after 3 wks. | Weight of fresh plant (g) | Root evaluation (1–4) |
| --- | --- | --- | --- | --- |
| 1 | 10 mg | 25 | 20 g | 4 |
|   | 20 mg | 22 | 19 g | 4 |
|   | 30 mg | 23 | 19 g | 4 |
| 3 | 10 mg | 24 | 22 g | 4 |
|   | 20 mg | 24 | 24 g | 4 |
|   | 30 mg | 25 | 22 g | 4 |
| 8 | 10 mg | 19 | 12 g | 1 |
|   | 20 mg | 24 | 22 g | 4 |
|   | 30 mg | 25 | 22 g | 4 |
| 15 | 10 mg | 22 | 20 g | 4 |
|   | 20 mg | 23 | 20 g | 4 |
|   | 30 mg | 24 | 20 g | 4 |
| 17 | 10 mg | 23 | 24 g | 4 |
|   | 20 mg | 24 | 22 g | 4 |
|   | 30 mg | 24 | 26 g | 4 |
| 30 | 10 mg | 21 | 18 g | 1 |
|   | 20 mg | 24 | 24 g | 4 |
|   | 30 mg | 22 | 18 g | 4 |
|   | mg of active | Number of | Weight of | Root |

-continued

Root evaluation: 4 = white roots, without fungus necroses
3 = white roots, slight fungus necroses
2 = brown roots, more intense fungus necroses
1 = severe fungus necroses, roots rotted

| Comparative Agents | ingr. per liter of soil | sound peas after 3 wks. | fresh plant (g) | evaluation(1-4) |
|---|---|---|---|---|
| 5-ethoxy-3-tri- | 10 mg | 12 | 10 g | 1 |
| chloromethyl-1,2,4- | 20 mg | 21 | 16 g | 4 |
| thiadiazole | 30 mg | 19 | 14 g | 4 |
| 1,4-dichloro-2,5-dimethoxy-benzene | 200 mg | 2 | 1 g | 1 |
| N-(trichloromethyl)thio)-cyclohex-4-ene-1,2-dicarboximide | 200 mg | 13 | 6 g | 1 |
| Zinc ethylene-bis-dithiocarbamate | 200 mg | 14 | 7 g | 1 |
| Steamed soil | — | 20 | 16 g | 4 |
| Untreated soil | — | 0 | 0 g | — |

It follows from the findings at hand that even the 1,2,4-thiadiazole derivative known to have specific Pythium action does not exceed the action of the compounds according to the invention against this fungus, but is, on the contrary, in part somewhat less effective than these.

EXAMPLE 3

Steamed compost soil was inoculated with mycelium of Rhizoctonia solani. After homogeneous mixture of the products with the infested soil, the products were present in the form of 20% powder preparations, the seeding of 25 grains of marrow peas of the variety "Miracle of Kelvedon" per concentration was effected without waiting period in clay dishes holding 1 liter of soil. The table lists the number of germinated sound peas, the weight of the fresh plant, and a root evaluation after a cultivation period of three weeks at 22°-25° C.

The above test results prove the superior action of the compounds according to the invention against Rhizoctonia in comparison with commercial products.

EXAMPLE 4

Comparison of the fungistatic and fungicidal action on Pythium ultimum when using preparations with varyng active ingredient percentages on siliceous clay. Steamed compost soil was inoculated with mycelium of Pythium ultimum. After forming a homogeneous mixture of the products with the infested soil, the products were present in the form of 20% powder preparations, the seeding of 25 grains of marrow peas of the variety "Miracle of Kelvedon" per concentration in clay dishes holding 1 liter of soil followed without a waiting period. In the table is stated the fresh number of germinated sound peas, the weight of the fresh plant, and a root evaluation after a cultivation period of three weeks at 22°-25° C.

| Compound No. | mg of active ingr. per liter of soil | Number of sound peas after 3 wks. | Weight of fresh plant (g) | Root evaluation (1-4) |
|---|---|---|---|---|
| 3 | 10 mg | 0 | 0 g | — |
|  | 20 mg | 2 | 2 g | 1 |
|  | 30 mg | 22 | 21 g | 4 |
| 8 | 10 mg | 21 | 17 g | 4 |
|  | 20 mg | 24 | 17 g | 4 |
|  | 30 mg | 24 | 17 g | 4 |
| 9 | 10 mg | 22 | 18 g | 4 |
|  | 20 mg | 22 | 16 g | 4 |
|  | 30 mg | 23 | 17 g | 4 |
| 17 | 10 mg | 0 | 0 g | — |
|  | 20 mg | 23 | 14 g | 4 |
|  | 30 mg | 22 | 14 g | 4 |
| 21 | 10 mg | 17 | 11 g | 4 |
|  | 20 mg | 24 | 17 g | 4 |
|  | 30 mg | 24 | 17 g | 4 |
| 23 | 10 mg | 13 | 9 g | 1 |
|  | 20 mg | 21 | 17 g | 3 |
|  | 30 mg | 24 | 20 g | 4 |
| Comparative Agents |  |  |  |  |
| 1,4-dichloro-2,5-dimethoxy-benzene | 10 mg | 0 | 0 g | — |
|  | 20 mg | 0 | 0 g | — |
|  | 30 mg | 21 | 18 g | 4 |
|  | 40 mg | 22 | 18 g | 4 |
| Pentachloronitrobenzene | 50 mg | 4 | 4 g | 1 |
|  | 100 mg | 25 | 15 g | 4 |
| Steamed soil | — | 20 | 17 g | 4 |
| Untreated soil | — | 0 | 0 g | — |

| Compound No. 17 | mg active ingr. per liter of soil | Number of sound peas after 3 weeks | Weight of fresh plant (g) | Root evaluation (1-4) |
|---|---|---|---|---|
| 20% | 6 mg | 22 | 17 | 2 |
| formulation | 10 mg | 24 | 16 | 4 |
| 10% | 6 mg | 24 | 15 | 1 |
| formulation | 10 mg | 22 | 24 | 4 |
| 5% | 6 mg | 12 | 9 | 1 |
| formulation | 10 mg | 24 | 20 | 4 |
| Steamed soil | — | 24 | 20 | 4 |
| Untreated soil | — | 0 | 0 | — |

This experiment shows that with concentrations of 6 mg of active ingredient per liter of soil, considerable fungistatic effects are attained. At a dosage of 10 mg of active ingredient per liter of soil, the action of the tested formulations is optimal.

EXAMPLE 5

Steamed compost soil was inoculated with a spore suspension of Fusarium oxysporum f. callistephi. After homogeneous mixture of the products with the infested soil, the products were present as 20% powder preparations, and after a waiting period of 8 days, there were set out per concentration 4 seedlings of Callistephus chinesis, master aster "Sun Ray" as host plants. The following table states the number of attacked plants after three weeks.

| Compound No. | mg of active ingredient per liter of soil | Number of attacked plants after 3 weeks |
|---|---|---|
| 3 | 50 mg | 0 |
|  | 100 mg | 0 |
| 8 | 50 mg | 0 |
|  | 100 mg | 0 |
| 9 | 50 mg | 0 |
|  | 100 mg | 0 |
| 17 | 50 mg | 0 |
|  | 100 mg | 0 |
| 19 | 50 mg | 0 |
|  | 100 mg | 0 |
| 21 | 50 mg | 0 |
|  | 100 mg | 0 |
| 22 | 50 mg | 0 |
|  | 100 mg | 0 |
| 25 | 50 mg | 0 |
|  | 100 mg | 0 |
| Comparative Agents |  |  |
| N-(trichloromethyl-thio)- | 50 mg | 4 |
| cyclohex-4-ene-1,2-dicar- | 100 mg | 4 |
| boximide | 200 mg | 4 |
| 5-ethoxy-3-trichloromethyl- | 50 mg | 4 |
| 1,2,4-thiadiazole | 100 mg | 4 |
|  | 200 mg | 4 |
| 1,4-dichloro-2,5-dimethoxy- | 50 mg | 4 |
| benzene | 100 mg | 4 |
|  | 200 mg | 4 |
| Steamed soil |  | 0 |
| Untreated soil |  | 4 |

This experiment, too, shows the superiority of the compounds according to the invention over commercial fungicides.

EXAMPLE 6

Cotton seeds disinfected with 10% formulations were seeded in normal compost soil (Damping-off Fungi), 25 grains per concentration. After a cultivation time of 15 days at 22°-25° C, the number of germinated sound cotton seedlings and their weight as fresh plants were determined.

| Compound No. | Active ingr. per kg of seed | Sound plants in % | Weight of fresh plant |
|---|---|---|---|
| 3 | 100 mg | 100% | 29 g |
| 8 | 100 mg | 96% | 29 g |
| 17 | 100 mg | 100% | 23 g |
| 21 | 100 mg | 100% | 33 g |
| Steamed soil, seed without disinfection |  | 100% | 27 g |
| Untreated soil, seed without disinfection |  | 50% | 14.5 g |

From this experiment, the excellent effectiveness of the compounds according to the invention when used as disinfectants for cotton seed is evident.

EXAMPLE 7

The fungicidal action of the agents according to the invention was tested in artificial nutrient media against plant-pathogenic fungi in Petri dishes (agar test). The procedure was to sterilize the medium consisting of 2% malt extract and 1.5% agar-agar powder. Before the solidification of the medium, the active substances were added to it, mixing thoroughly, so that the medium received 10 parts of active substance per million (ppm). After the solidification of the medium, the latter was inoculated with a platinum dropper which contained 100 spores each of the fungi to be tested, and after five days at 22° C, an evaluation was made by measuring the diameter of the colonies in mm.

| Compound No. | Aspergilus niger | Botrytis cinerea | Colletotrichum gloeosporioides | Helminthosporium sativum | Stemphylium ilicis |
|---|---|---|---|---|---|
| 1 | 0 | 0 | 0 | 0 | 0 |
| 3 | 50 | 36 | 0 | 0 | 0 |
| 7 | 0 | 22 | 0 | 0 | 0 |
| 8 | 0 | 0 | 0 | 0 | 0 |
| 9 | 0 | 0 | 0 | 0 | 0 |
| 10 | 0 | 0 | 0 | 0 | 0 |
| 12 | 0 | 0 | 0 | 0 | 0 |
| 13 | 0 | 13 | 0 | 0 | 0 |
| 17 | 0 | 0 | 0 | 0 | 0 |
| 18 | 0 | 13 | 41 | 0 | 0 |
| 19 | 0 | 0 | 0 | 0 | 0 |
| 21 | 0 | 0 | 0 | 0 | 0 |
| 22 | 0 | 0 | 0 | 0 | 0 |
| 23 | 0 | 0 | 0 | 0 | 0 |

-continued

| | | | | | |
|---|---|---|---|---|---|
| 24 | 0 | 0 | 0 | 0 | 0 |
| 25 | 0 | 0 | 0 | 0 | 0 |
| 26 | 0 | 0 | 0 | 0 | 0 |
| 27 | 0 | 0 | 0 | 0 | 0 |
| 28 | 0 | 0 | 0 | 0 | 0 |
| 29 | 19 | 18 | 0 | 0 | 0 |
| 32 | 0 | 0 | 0 | 0 | 0 |
| Comparative Agents | | | | | |
| zinc ethylene-bis-dithiocarbamate | 78 | 36 | 81 | 50 | 55 |
| Control | 100 | 100 | 100 | 100 | 100 |

The superior fungicidal action as against the known comparative agents is clearly to be seen from the above results.

EXAMPLE 8

The products as 20% powder preparations were homogeneously admixed with a compost soil heavily infested by root gal nematodes. Without a waiting period, 20 cucumber seeds per concentration were seeded. After a cultivation time of 30 days at a temperature of 23°–25° C, the nematocidal action was evaluated by counting the root galls formed in the waterbath. The following table states the reduction of attack in percent. In the control, an average of 90 root galls per seedling had formed.

| Compound No. | Active substance per liter of soil | Nematocidal action in % (Meloidogyne incognita) |
|---|---|---|
| 3 | 40 mg | 100% |
|   | 60 mg | 100% |
| 4 | 40 mg | 96% |
|   | 60 mg | 99% |
| 5 | 40 mg | 90% |
|   | 60 mg | 98% |
| 17 | 40 mg | 90% |
|    | 60 mg | 94% |
| 18 | 40 mg | 61% |
|    | 60 mg | 90% |
| 19 | 40 mg | 72% |
|    | 60 mg | 82% |

The findings of this experiment show the nematocidal action of the compounds according to the invention.

EXAMPLE 9

Control of Pyrenochaeta lycopersici, corky root disease of the tomato.

On a naturally invested open field area, 2-dichloromethyl-5-methylsulfonyl-1,3,4-thiadiazole was scattered as a 10% granulate formulation and hoed in 20 cm deep. At the time of treatment, the sandy loam had a relative soil moisture of 10%. After a reaction period of three weeks, tomato plants of the variety "Ronald-M" which were 8 weeks old were set out at a distance from each other of 50 × 70 cm. The harvest results indicated in the table are average values of 40 plants per lot and refer to harvested ripe tomatoes.

| g of active ingr. per square meter | Yield per plant | Tomatoes per plant | Weight of single tomato |
|---|---|---|---|
| 20 g | 2209 g (213%) | 28 (165%) | 78 g (130%) |
| 10 g | 1774 g (171%) | 27 (159%) | 66 g (110%) |
| 0 g | 1036 g (100%) | 17 (100%) | 60 g (100%) |

EXAMPLE 10

Control of Thielaviopsis basicola on tobacco.

A 10% powder preparation of 2-trifluoromethyl-5-methylsulfonyl-1,3,4-thiadiazole was homogeneously admixed to a soil heavily infested by Thielaviopsis basicola. After a reaction time of one week, tobacco seedlings of the variety Nicotiana tabacum var. "White Burley" were set out and cultivated for five weeks in the greenhouse at 22°–32° C. The attack and weight of the fresh plant are evident from the table.

| Active ingr. per liter of soil | Attack 0–5 | Weight of fresh plant (leaves and stems) | Weight of roots (air-dry) |
|---|---|---|---|
| 20 mg | 0.5 | 115 g | 11 g |
| 30 mg | 0 | 118 g | 11 g |
| 40 mg | 0 | 104 g | 9 g |
| Steamed soil | 0 | 111 g | 12 g |
| Infested soil | 5 | 21 g | 0.5 g |

0 = no attack
1 = very slight attack
2 = slight attack
3 = medium attack
4 = strong attack
5 = very strong attack

Example 11

| Fungicidal effect of | 2-trifluoromethyl-5-methylsulfonyl-1,3,4-thiadiazole (1) |
|---|---|
| | 2-trifluoromethyl-5-ethylsulfonyl-1,3,4-thiadiazole (36) |
| | 2-trifluoromethyl-5-methylsulfinyl-1,3,4-thiadiazole (35) |
| | 2-trifluoromethyl-5-ethylsulfinyl-1,3,4-thiadiazole (36) | in the vapor phase:

Nutrient medium inoculated with mycelium of Pythium ultimum or Rhizoctonia solani in open Petri dishes was placed in glass vessels 12 cm tall. First the quantity of product as a 10% powder preparation had been placed on the bottom of the glasses. After a reaction time of 3 days (Pythium) and 5 days (Rhizoctonia) at a temperature of 22° C in the covered glass vessel, the mycelium growth was evaluated. While in the untreated glasses, the Petri dishes were completely grown over with Pythium or Rhizoctonia, the treatments showed no mycelium growth even at a dose of 1 mg of active ingredient per liter.

EXAMPLE 12

Production of a dry disinfectant.

The following constituents are mixed together:

10% by weight of 2-trifluoromethyl-5-methylsulfonyl-1,3,4-thiazole; 87.8% by weight of talcum; 0.2% by weight of new fuchsine; 2% by weight of paraffin oil.

The mixture is then ground in an air jet mill to a finely dispersed powder. This preparation may be used as disinfectant as described above.

What is claimed is:

1. The compound 2-trichloromethyl-5-methylsulfinyl-1,3,4-thiadiazol.

* * * * *